(12) United States Patent
Chen

(10) Patent No.: US 7,977,346 B2
(45) Date of Patent: Jul. 12, 2011

(54) SPIRO COMPOUNDS AND METHODS OF USE

(76) Inventor: Guoqing Paul Chen, Moorpark, CA (US)

( * ) Notice: Subject to any disclaimer, the term of this patent is extended or adjusted under 35 U.S.C. 154(b) by 1190 days.

(21) Appl. No.: 11/647,823

(22) Filed: Dec. 30, 2006

(65) Prior Publication Data

US 2007/0167470 A1    Jul. 19, 2007

Related U.S. Application Data

(60) Provisional application No. 60/759,601, filed on Jan. 17, 2006.

(51) Int. Cl.
*A01N 43/54* (2006.01)
*A61K 31/517* (2006.01)
(52) U.S. Cl. ............... 514/266.1; 544/283
(58) Field of Classification Search .......... 544/283; 514/266.1
See application file for complete search history.

(56) References Cited

U.S. PATENT DOCUMENTS

| | | | |
|---|---|---|---|
| 5,137,892 | A | 8/1992 | Chu |
| 5,591,748 | A | 1/1997 | Badger |
| 5,770,599 | A | 6/1998 | Gibson |
| 6,197,974 | B1 | 3/2001 | Abbott |
| 2002/0173501 | A1 | 11/2002 | Ledoussal |

FOREIGN PATENT DOCUMENTS

| | | |
|---|---|---|
| EP | 0341493 | 11/1989 |
| EP | 357047 | 3/1990 |
| EP | 611137 | 8/1994 |
| EP | 0623585 | 11/1994 |
| JP | 04342564 | 11/1992 |
| JP | 05221947 | 8/1993 |
| JP | 06145167 | 5/1994 |
| JP | 2002053536 | 2/2002 |
| JP | 2002069072 | 3/2002 |
| JP | 2002201191 | 7/2002 |
| JP | 2004099609 | 4/2004 |
| WO | WO9221659 | 12/1992 |
| WO | WO9510519 | 4/1995 |
| WO | WO9639407 | 12/1996 |
| WO | WO0153273 | 7/2001 |
| WO | WO03014108 | 2/2003 |
| WO | WO2005026165 | 3/2005 |
| WO | WO2006073167 | 7/2006 |
| WO | WO2006123767 | 11/2006 |
| WO | WO2006123792 | 11/2006 |
| WO | WO2007037330 | 4/2007 |

OTHER PUBLICATIONS

Vippagunta et al., "Crystalline Solids", Adv. Drug Del. Rev., 48 (2001) 3-26.*
JMC 37, 3344(1994): Kimura, Youichi; ACS Publication.
Tetrahedron Letter, 41, 8173-8176; Storey, John; Elsevier Science Publication.
JACS, 119, 7625-7616 (1997); Yamaura, Yousuke; ACS Publication.
Heterocycles, 52, 595-598; Elsevier Science Publication.

* cited by examiner

*Primary Examiner* — James O. Wilson
*Assistant Examiner* — Paul V. Ward

(57) ABSTRACT

The present invention relates to spiro compounds of formula I, processes for their preparation, pharmaceutical compositions containing them as active ingredient, methods for the treatment of disease states such as cancers associated with protein tyrosine kinases, especially epidermal growth factor (EGF) and vascular endothelial growth factor (VEGF), to their method of use as medicaments and to their method of use in the manufacture of medicaments for use in the production of inhibition of tyrosine kinase reducing effects in warm-blooded animals such as humans.

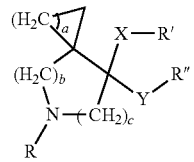

Formula I

10 Claims, No Drawings

SPIRO COMPOUNDS AND METHODS OF USE

This application claims the benefit of U.S. Provisional Application No. 60/759,601 filed on Jan. 17, 2006.

FIELD OF THE INVENTION

The present invention relates to spiro compounds, processes for their preparation, pharmaceutical compositions containing them as active ingredient, methods for the treatment of disease states such as cancers associated with protein tyrosine kinases, especially epidermal growth factor (EGF) and vascular endothelial growth factor (VEGF), to their method of use as medicaments and to their method of use in the manufacture of medicaments for use in the production of inhibition of tyrosine kinase reducing effects in warm-blooded animals such as humans.

BACKGROUND OF THE INVENTION

Protein tyrosine kinases have been identified as key players in cellular regulation. They are involved in immune, endocrine, and nervous system physiology and pathology and thought to be important in the development of many cancers. Protein tyrosine kinases represent a diverse and rapidly expanding superfamily of protein, including both transmembrane receptor tyrosine kinases and soluble cytoplasmic enzymes also known as nonreceptor tyrosine kinases.

Receptor tyrosine kinases are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. It has also been shown that epidermal growth factor receptor (EGFR) which possesses tyrosine kinase activity is mutated and/or over expressed in many human cancers such as brain, lung, squamous cell, bladder, gastric, breast, head and neck, oesophageal, gynecological and thyroid tumors. EGFR is the archetypal member of receptor tyrosine kinase family comprised of four closely related receptors called EGFR, HER2 (human EGF-related receptor), HER3 and HER4 (Pinkas-Kramarski R, Eilam R, Alroy I, Levkowitz G, Lonai P, Yarden Y. Differential expression of NDF/neuregulin receptors ErbB-3 and ErbB-4 and involvement in inhibition of neuronal differentiation. Oncogene 1997; 15:2803-2815). All of these transmembrane receptors contain an intrinsic kinase activity that modifies tyrosine residues on the receptor itself as well as on downstream signaling molecules. This kinase activity is stimulated when members of the EGF family of growth factors bind to the receptor. Ligand-induced EGFR activation initiates a signaling cascade that activates gene expression and induces cellular responses such as cell cycle progression or differentiation. Aberrant activation of this highly regulated signaling pathway is believed to contribute to many tumorigenic processes, including enhanced cellular proliferation, protection from apoptosis, tumor cell invasion and metastasis (Huang S M, Harari P M. Epidermal growth factor receptor inhibition in cancer therapy: biology, rational and preliminary clinical results. Invest New Drugs 1999; 17:259-269).

Each receptor is composed of three domains—an extracellular ligand-binding domain, a transmembrane domain, and an intracellular tyrosine kinase domain. The active receptor is a dimmer, which can be formed by combinations of identical receptor pairs (homodimerization) or different receptor pairs (heterodimerization). EGFR has two main ligands, epidermal growth factor (EGF) and transforming growth factor (TGF). Following binding of a ligand, the receptor dimerizes, which results in activation of the intracellular tyrosine kinase. This begins a number of phosphorylation events that, in turn, initiate a cascade of intracellular signaling process.

Accordingly, it has been recognized that inhibitors of receptor tyrosine kinases are useful as a selective inhibitors of the growth of mammalian cancer cells.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma. Tumor angiogenesis, the formation of new blood vessels and their permeability is primarily regulated by (tumor-derived) vascular endothelial growth factor (VEGF), which acts via at least two different receptors: VEGF-R1 (fms-like tyrosine kinase, Flt-1); and VEGF-R2 (kinase domain region, KDR/fetal liver kinase-1, Flk-1). The VEGF KDR receptor is highly specific for vascular endothelial cells (for review, see: Farrara et al. *Endocr. Rev.* 1992, 13, 18; Neufield et al. *FASEB J.* 1999, 13, 9).

VEGF is another kind of receptor protein tyrosine kinases. A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth.

It has now been found that spiro compounds of formula I, described below, are a new class of compounds that have advantageous pharmacological properties and inhibit the activity of tyrosine kinases, for example, the activity of the EGFR and VEGFR tyrosine kinases, the activity of other receptor tyrosine kinases, such as c-kit, PDGF, FGF, SRC etc. They may also be irreversible inhibitors of tyrosine kinase.

Examples of spiro compounds that are similar in structure to those of the present invention are disclosed in the following literatures: WO9510519, WO9639407, WO0153273, WO03014108, WO20026073167, JP05221947, JP2004099609, EP0341493, EP0357047, EP0623585, EP611137, JMC 37, 3344 (1994), Tetrahedron Letter, 41, 8173-8176, JACS, 119, 7615-7616 and Heterocycles, 52, 595-598 with the following structures:

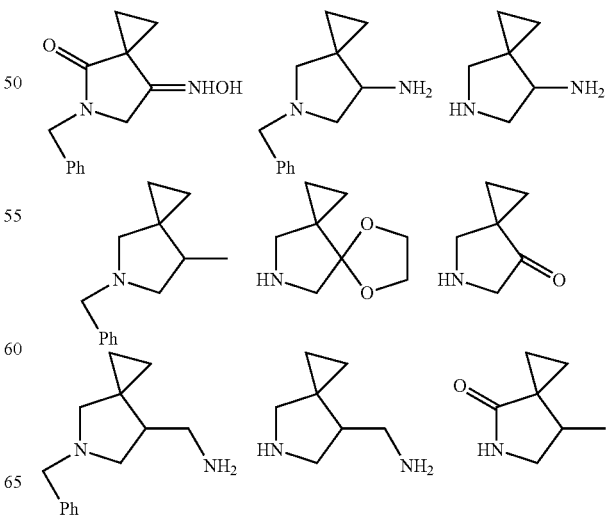

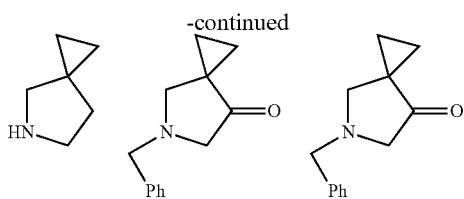

Examples of non-spiro compounds of quinazoline derivatives that are similar in structure to those of the present invention are disclosed in the following patent applications: EP0357047, EP 0566226, EP 0602851, EP 0635507, EP 0635498, EP 0520722, WO9633980, WO9738983, WO9738994, WO0047212, WO0121596, WO0132651, and WO02092577.

SUMMARY OF THE INVENTION

The present invention relates to spiro compounds of formula I

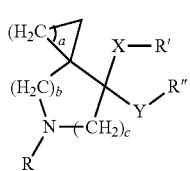

Formula I

Wherein
a is 1, 2, 3, 4 or 5;
b and c are each independently 1, 2, or 3;
When X and Y are selected from (i) X combines Y to be an oxygen or methylene, (ii) X is hydrogen, Y is hydrogen, (iii) X is hydrogen, Y is hydroxy or its optical isomer; R' and R" are not presented;
When X and Y are selected from (iv) X is hydrogen, Y is O, S or its optical isomer position, (v) X and Y are both O, or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents;
R is selected from:

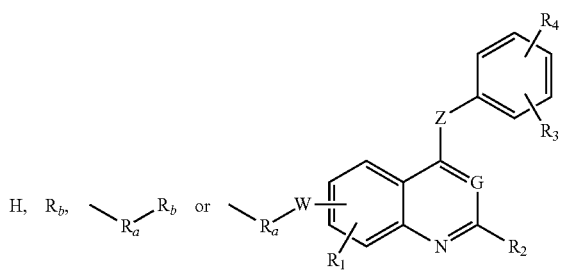

$R_a$ is selected from lower alkylenyl, lower alkenlenyl or lower alkynlenyl;
$R_b$ is selected from halogen, hydroxy, methanesulfonate, toluenesulfonate, aryl or heterocyclyl;
W is selected from O, S, —$NR_c$ or —$CHR_c$;
G is selected from N, —C—CN or —$CR_c$;
Z is selected from O, S, —$NR_d$ or —$CHR_d$;
$R_c$ is selected from H, lower alkyl;
$R_d$ is selected from H, lower alkyl, amino or alkylamino;
$R_1$, $R_3$, and $R_4$ are each independently selected from H, halogen, halogeno-lower alkyl, lower alkyl, lower alkoxy, lower alkoxyalkoxy, lower alkenyl, or lower alkynyl;
$R_2$ is selected from H, halogen, halogeno-lower alkyl or lower alkyl;
Or a pharmaceutically acceptable salt thereof.

DETAILED DESCRIPTION OF THE INVENTION

The present invention is the direct to novel compounds which can inhibit protein tyrosine kinases, especially EGFR and VEGFR tyrosine kinases, and methods of use of these compounds for inhibition of tyrosine kinases in the treatment of a neoplastic or proliferative or inflammatory diseases, or transplantation disorders which are all caused by excess or inappropriate tyrosine kinases in a mammal in need thereof.
In a compound of formula I:
Wherein
a is 1, 2, 3, 4 or 5; preferably a is 1, 2 or 3;
b and c are each independently 1, 2, or 3; preferably b and c are 1 or 2;
When X and Y are selected from (i) X combines Y to be an oxygen or methylene, (ii) X is hydrogen, Y is hydrogen, (iii) X is hydrogen, Y is hydroxy or its optical isomer; R' and R" are not presented; these moieties are selected from ketone, methylene as well as hydroxy and its optical isomers;
When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents; preferably these moieties are selected from alkoxy or its optical isomers, and alkyl or cyclic ketal, thioketal, thioxolane which may be unsubstituted or substituted with lower alkyl, aryl or heterocyclyl;
R is selected from:

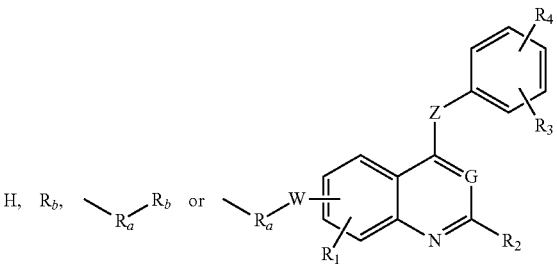

$R_a$ is selected from lower alkylenyl, lower alkenlenyl or lower alkynlenyl; preferably $R_a$ is lower alkylenyl;
$R_b$ is selected from halogen, hydroxy, methanesulfonate, toluenesulfonate, aryl or heterocyclyl; preferably $R_b$ is halogen or hydroxy;
W is selected from O, S, —$NR_c$ or —$CHR_c$; preferably W is O,
G is selected from N, —C—CN or —$CR_c$; preferably G is N;
Z is selected from O, S, —$NR_d$ or —$CHR_d$; preferably Z is O or —$NR_d$;
$R_c$ is selected from H, lower alkyl; preferably $R_c$ is H;

$R_d$ is selected from H, lower alkyl, amino or alkylamino; preferably $R_d$ is H;

$R_1$, $R_3$, and $R_4$ are each independently selected from H, halogen, halogeno-lower alkyl, lower alkyl, lower alkoxy, lower alkoxyalkoxy, lower alkenyl, or lower alkynyl; preferably $R_1$, $R_3$, and $R_4$ are each independently halogen, lower alkyl or lower alkoxy;

$R_2$ is selected from H, halogen, halogeno-lower alkyl or lower alkyl; preferably $R_2$ is H or fluorine;

Or a pharmaceutically acceptable salt thereof.

The term "lower alkylenyl", as used herein, unless otherwise indicated, includes 1 to 6 saturated —CH$_2$— radicals.

The term "lower alkenlenyl", as used herein, unless otherwise indicated, includes lower alkylenyl groups, as defined above, having at least one carbon-carbon double bond, such as —CH$_2$—CH=CH—.

The term "lower alkynlenyl", as used herein, unless otherwise indicated, includes lower alkylenyl groups, as defined above, having at least one carbon-carbon triple bond, such as —CH$_2$—C≡C—.

The term "halogen", as used herein, unless otherwise indicated, includes fluoro, chloro, bromo or iodo. Preferred halogens are fluoro, chloro and bromo.

The term "halogeno-lower alkyl", as used herein, unless otherwise indicated, includes 1 to 6 halogen substituted lower alkyl, such as trifluoromethyl, pentafluoroethyl.

The term "lower alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "lower alkenyl", as used herein, unless otherwise indicated, includes lower alkyl groups, as defined above, having at least one carbon-carbon double bond, such as —CH$_2$—CH=CH$_2$.

The term "lower alkynyl", as used herein, unless otherwise indicated, includes lower alkyl groups, as defined above, having at least one carbon-carbon triple bond, such as —CH$_2$—C≡CH.

The term "lower alkylhydroxy", as used herein, unless otherwise indicated, includes—lower alkyl-OH groups wherein lower alkyl is as defined above The term "lower alkoxy", as used herein, unless otherwise indicated, includes —O— lower alkyl groups wherein lower alkyl is as defined above.

The term "lower alkoxyalkoxy", as used herein, unless otherwise indicated, includes —O— lower alkyl-O— lower alkyl groups wherein lower alkyl is as defined above, such as —OCH$_2$CH$_2$OCH$_3$.

The term "aryl", as used herein, unless otherwise indicated, includes an organic radical derived from an aromatic hydrocarbon by removal of one hydrogen, such as phenyl or naphthyl, preferably phenyl, and is unsubstituted or substituted by one or two substituents, selected from halogen, halogeno-lower alkyl, lower alkyl, lower alkenyl, lower alkynyl, cyano, lower alkylcyano, hydroxy, lower alkoxy, carboxy, carboxyalkyl, amino, carbamoyl, cabamate, ureido, mercapto, sulfo, lower alkysulfinyl, lower alkanesulfonyl, sulfonamide; aryl includes one aromatic ring fused with an aliphatic ring, such as a saturated or partially saturated ring, such as tetrahydronaphthyl.

The term "heterocyclyl", as used herein, unless otherwise indicated, includes non-aromatic, single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. examples of heterocyclyl groups include but not limited: azetidine, pyrrolidine, pyrrolidione, piperidine, piperidinone, piperazine, morpholine, oxetane, tetrahydrofuran, tetrahydropyran, imidazolidine, pyrazolidine and hydantoin, pyrrole, indole, pyrazole, indazole, trizole, benzotrizole, imidazole, benzoimdazole, thiophene, benzothiophene, thiozole, benzothiozole, furan, benzofuran, oxazole, bezoxazole, isoxazole, tetrazole, pyridine, pyrimidine, trizine, quinoline, isoquinoline, quinazoline, indoline, indolinone, benzotetrahydrofuran, tetrahydroquinoline, tetrahydroisoquinoline, methylene-dioxyphenyl. The heterocyclic and heterocyclic rings may be optionally substituted and substituents selected from the group defined above as substituents for aryl.

Several in vitro tyrosine kinase inhibition activities can be measured according to the description in Rewcastle, G W, J. Med. Chem. 1996, 39, 918-928 and Edwards M, International Biotechnology Lab 5 (3), 19-25, 1987. Oncogene, 1990, 5: 519-524. The Baculovirus Expression System: A Laboratory Guide, L. A. King 1992. Sambrook et al, 1989, Molecular cloning—A Laboratory Manual, 2nd edition, Cold Spring Harbour Laboratory Press. O'Reilly et al, 1992, Baculovirus Expression Vectors—A Laboratory Manual, W. H. Freeman and Co, New York.

Receptor tyrosine kinase can be obtained in partially purified form from A-431 cells similar to those described by Carpenter et al., J. Biol. Chem., 1979, 254, 4884, Cohen et al., J. Biol. Chem., 1982, 257, 1523 and by Braun et al., J. Biol. Chem., 1984, 259, 2051. Some of these tests can also be contracted with Upstate Ltd for screening.

The following in vitro results are activities of some compounds in present invention against human tumor NSCLC A549 cell line and colon LOVO cell line in MTT assay.

|  | A549 (IC50, nM) | LOVO (IC50, nM) |
| --- | --- | --- |
| Example 20 | 0.0619 | 0.0375 |
| Example 21 | 0.0421 | 0.139 |
| Example 22 | 0.0359 | 0.0329 |
| Example 23 | 0.0893 | 0.219 |
| Example 24 | 0.0375 | 0.165 |
| Example 25 | 0.0573 | 0.0954 |
| Example 26 | 0.091 | 0.0376 |
| Example 27 | 0.212 | 0.0978 |
| Example 28 | 0.096 | 0.0376 |
| Example 29 | 0.104 | 0.0934 |
| Example 30 | 0.0749 | 0.0272 |
| Example 31 | 0.0546 | 0.098 |
| Example 32 | 0.028 | 0.032 |
| Example 33 | 0.0519 | 0.118 |
| Example 34 | 0.034 | 0.171 |
| Example 35 | 0.0402 | 0.0318 |
| Example 36 | 0.022 | 0.057 |
| Example 37 | 0.132 | 0.0553 |
| Example 38 | 0.073 | 0.143 |
| Example 39 | 0.023 | 0.03 |
| Example 40 | 0.042 | 0.029 |
| Example 41 | 0.075 | 0.129 |

Animal antitumor activity testing can be conducted as follows:

The compounds were mixed with Tween 80 and 0.5% CMC as suspensions. Kunming male mice (19-21 g) were used. Ascitic fluid of mice HAC liver cancer was diluted with 0.9% NaCl solution (1:4), and injected 0.2 ml to each mouse subcutaneously. The whole animals (n=20) were separated evenly as test and control group randomly. The test group was administered drugs orally at 5-500 mg/Kg dosage once a day from second day after injection of tumor for seven days. The body weight of each animal was monitored everyday. The animals were sacrificed after ten days and each tumor was extracted and weighted for both groups and calculated the difference in percentage for antitumor activity.

The compounds were mixed with tween 80 and 0.5% CMC as suspensions. Nude female mice (17-19 g) were used. Ascitic fluid of human LOVO colon cancer was diluted with 0.9% NaCl solution (1:4), and injected 0.2 ml to each mouse subcutaneously. The whole animals (n=12) were separated even as test and control group randomly. The test group was administered drugs orally at 5-500 mg/Kg dosage once a day from second day after injection of tumor for eighteen days. The animals were sacrificed at 21st days and each tumor was extracted and weighted for both groups and calculated the difference in percentage for antitumor activity.

A compound of formula I can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

A compound of formula I can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula I. Suitable pharmaceutically acceptable salts will be apparent to those skilled in the art and include those described in *J. Pharm. Sci.*, 1977, 66, 1-19, such as acid addition salts formed with inorganic acid e.g. hydrochloric, hydrobromic, sulphuric, nitric or phosphoric acid; and organic acids e.g. succinic, maleic, acetic, fumaric, citic, tartaric, benzoic, p-toluenesulfonic, methanesulfonic or naphthalenesulfonic acid. Other salts may be used, for example in the isolation or purification of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extents to all isomeric forms including stereoisomers and geometic isomers of the compounds of formula (I) including enantimers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods know to those skilled in the art (see, for example: Chien; "transdermal Controlled Systemic Medications"; Marcel Dekker, Inc.; 1987. Lipp et al. WO 94/04157 3 Mar. 1994).

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.01 to 200 mg/Kg. The daily inhalation dosage regimen will preferably be from 0.01 to 200 mg/Kg of total body weight.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1-27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120-1127).

Representative illustrations of the preparation of the present invention are given in Scheme I-Scheme II. Those having skill in the art will recognize that the starting materials may be varied and additional steps may be employed to produce compounds encompassed by the present invention.

Scheme I
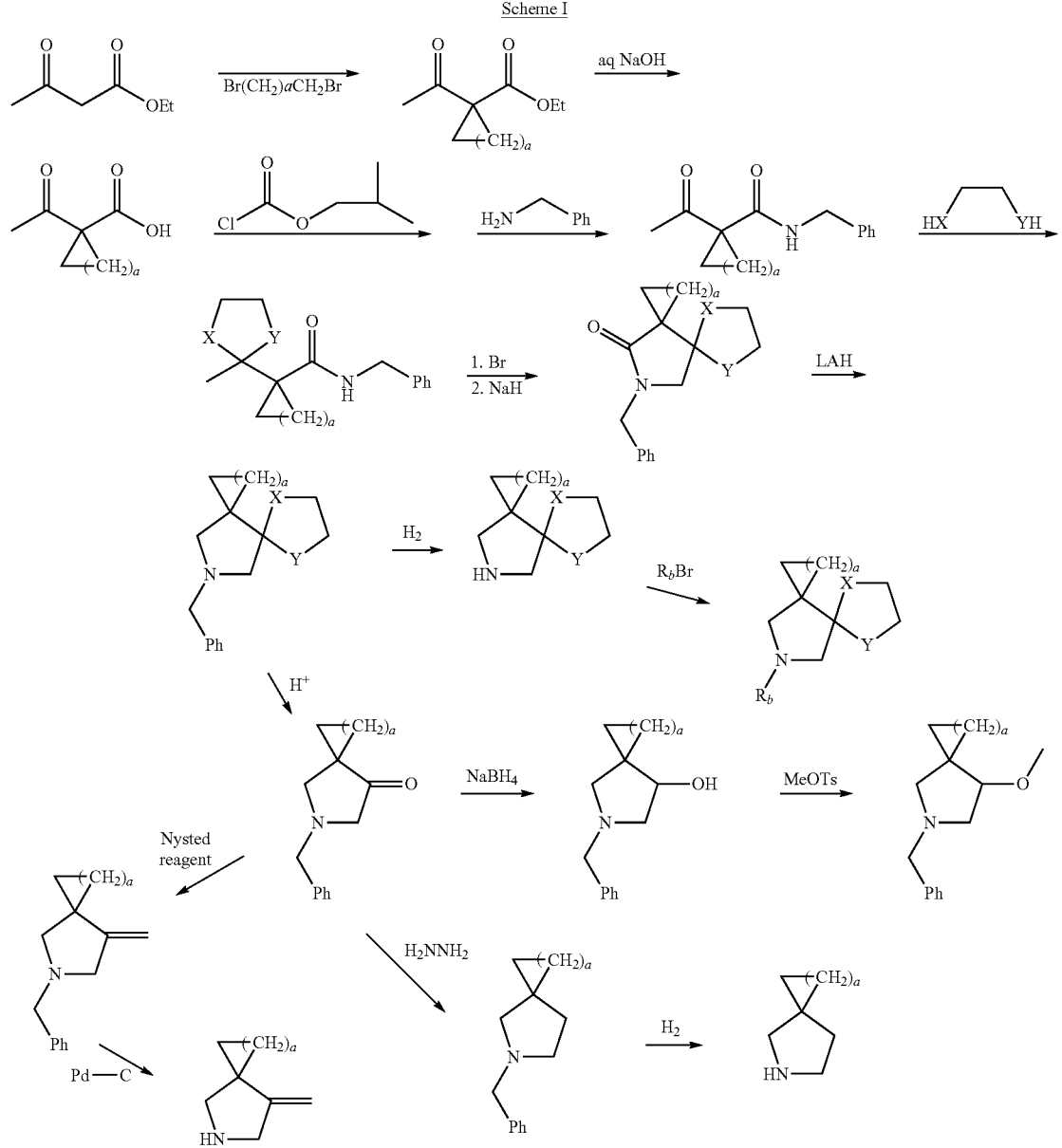
Scheme II
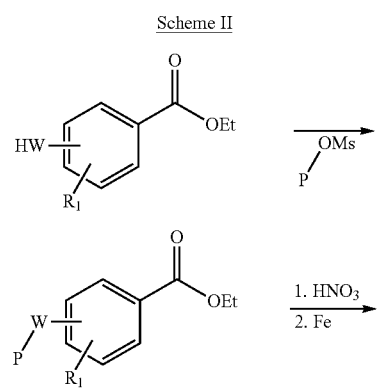
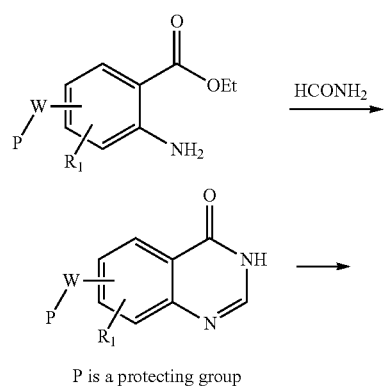
P is a protecting group

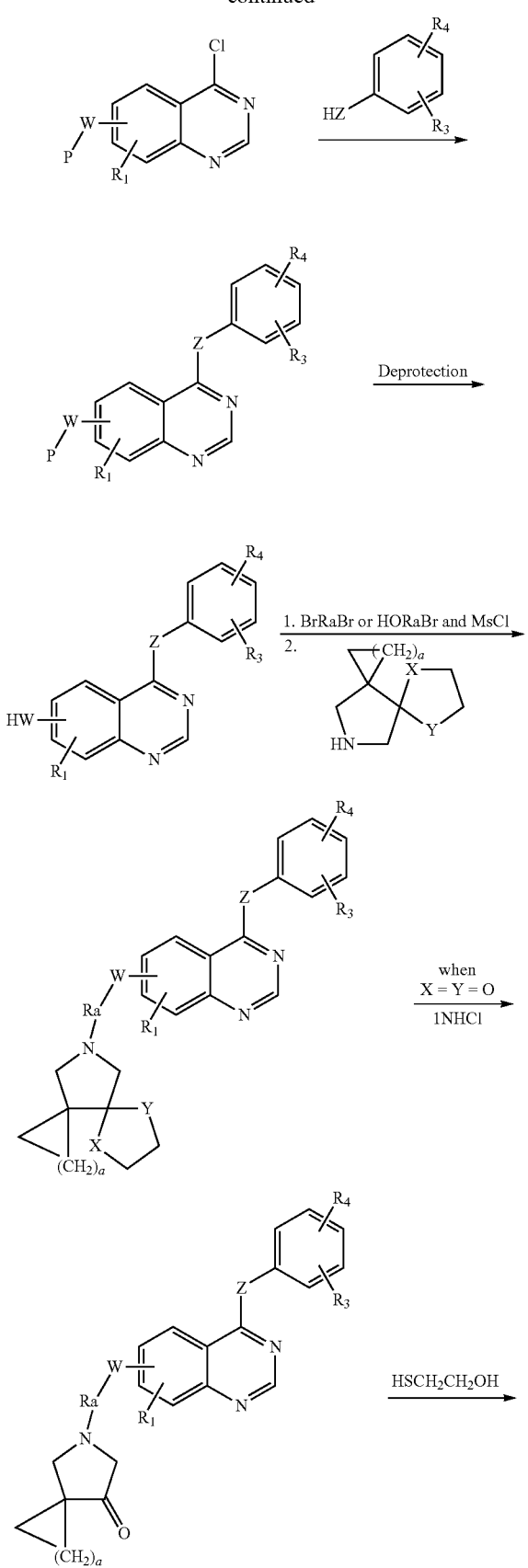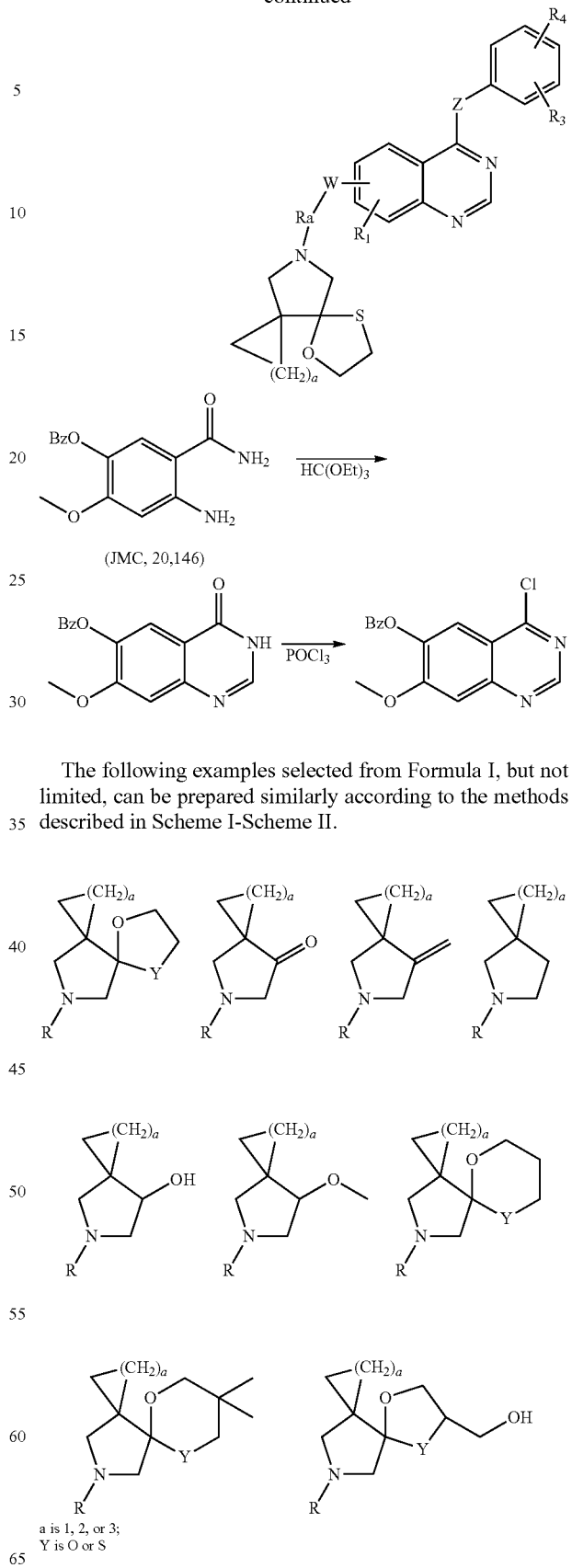
The following examples selected from Formula I, but not limited, can be prepared similarly according to the methods described in Scheme I-Scheme II.
a is 1, 2, or 3;
Y is O or S R is selected from: - - - : Substituting position

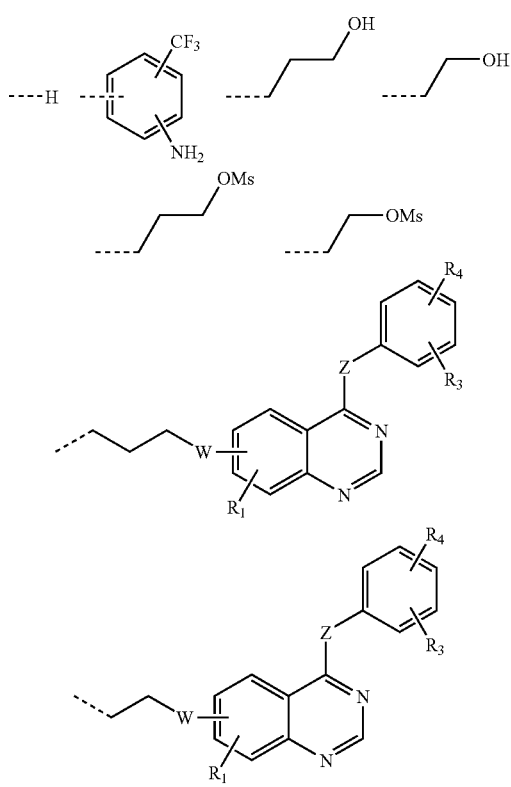

W is O,
Z is NH or O,
R₁ is ──OMe,
R₃ is 2-F, 4-F or 2,4-Di-Fluoro,
R₄ is 3-Cl or 4-Br.

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in their entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well know synthetic methods.

Representative methods for preparing intermediates of the invention are set forth below in the examples.

The following abbreviations have been used and others are all standard chemical formula representation.

| | |
|---|---|
| EtOH: ethanol | MeOH: methanol |
| RT: room temperature | TSA: n-Toluenesulfonic acid |
| DIPEA: diisopropylethylamine | DCM: Dichloro methane |
| EtOAc: ethyl acetate | DMF: N,N-dimethylformamide |
| MsCl: Methanesulfonyl chloride | TsOMe: methyl 4-methylbenzene-sulfonate |
| eq: equivalent, | g: gram, |
| ml: milliliter | μL: microliter |

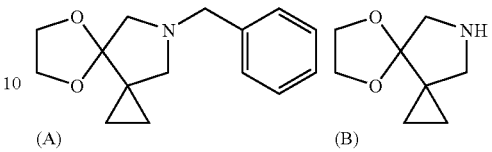

| (A) | (B) |
|---|---|
| 10-benzyl-5,8-Dioxa-10-azadispiro [2.0.4.3]undecane | 5,8-Dioxa-10-azadispiro[2.0.4.3] undecane |

Example 1

10-(2-hydroxyethyl)-5,8-Dioxa-10-azadispiro [2.0.4.3]undecane 10-benzyl-5,8-Dioxa-10-azadispiro[2.0.4.3]undecane (A) (1.0 g, similar prepared according to JMC 37, 3344) was mixed with Pd—C (10%, 600 mg) in EtOH (40 ml) and hydrogenated under H₂ at 50 psi for 5 hour. The reaction was filtered through Celite and evaporated to give 5,8-Dioxa-10-azadispiro[2.0.4.3]undecane (B).

The compound (B) (100 mg) was mixed with 2-Bromoethanol (100 mg) and K₂CO₃ (120 mg) in Acetonitrile. The reaction was refluxed overnight and filtered, the filtrate was evaporated and purified on silica gel column to give the titled product. Mass: (M+1), 200

Example 2

10-(3-hydroxypropyl)-5,8-Dioxa-10-azadispiro [2.0.4.3]undecane

The compound (B) (100 mg) was mixed with 3-Bromopropanol (120 mg) and K₂CO₃ (120 mg) in Acetonitrile. The reaction was refluxed overnight and filtered; the filtrate was evaporated and purified on silica gel column to give the titled product. Mass: (M+1), 214

Example 3

5-(2-hydroxyethyl)-5-azaspiro[2.4]heptan-7-one

The above product from Example 1 (100 mg) was mixed with 1N HCl (4 ml) and acetone (20 ml). The reaction was refluxed overnight and evaporated. The solution was basified with 2N NaOH and extracted with EtOAc. The combined organic layer was washed with H₂O followed by brine, dried over Na₂SO₄ and evaporated. The residue was purified by column chromatography to give title compound. Mass: (M+1), 156

Example 4

5-(3-hydroxypropyl)-5-azaspiro[2.4]heptan-7-one

The title compound was prepared by similar manner to Example 3, starting from the compound of Example 2. Mass: (M+1), 170

Example 5

5-(2-hydroxyethyl)-5-azaspiro[2.4]heptan-7-ol 5-(2-Hydroxyethyl)-5-azaspiro[2.4]heptan-7-one (100 mg) was dissolved into Methanol (8 ml) and stirred at RT. NaBH$_4$ (100 mg) was added to the reaction and stirred at RT for 30 minutes. The reaction was evaporated and purified by column chromatography to give title compound. Mass: (M+1), 158

Example 6

5-azaspiro[2.4]heptan-7-ol 5-benzyl-5-azaspiro[2.4]heptan-7-one was prepared by similar manner to Example 3, starting from 10-benzyl-5,8-Dioxa-10-azadispiro[2.0.4.3]undecane (A). 5-benzyl-5-azaspiro[2.4]heptan-7-one (100 mg) then was dissolved into Methanol (8 ml) and stirred at RT. NaBH$_4$ (100 mg) was added to the reaction and stirred at RT for 30 minutes. The reaction was evaporated and purified by column chromatography to give 5-benzyl-5-azaspiro[2.4]heptan-7-ol (85 mg) that was mixed with Pd—C (10%, 100 mg) in EtOH (15 ml) and hydrogenated under H$_2$ at 50 psi for 5 hour. The reaction was filtered through Celite and evaporated to give the title compound as an oil. Mass: (M+1), 115

Example 7

2-(5-azaspiro[2.4]heptan-5-yl)ethanol 5-benzyl-5-azaspiro[2.4]heptan-7-one (300 mg) was mixed with hydrazine (600 mg) and NaOH (300 mg) in H$_2$O (2 ml). The mixture was refluxed for overnight and purified by column chromatography to give 5-benzyl-5-azaspiro[2.4]heptane that was hydrogenated at 50 psi with Pd—C (10%, 80 mg) in EtOH (15 ml) for overnight followed by filtration through Celite to give 5-azaspiro[2.4]heptane. This product was mixed with 2-Bromoethanol and K$_2$CO$_3$ in Acetonitrile. The reaction was refluxed overnight and filtered, the filtrate was evaporated and purified on silica gel column to give the titled product. Mass: (M+1), 142

Example 8

3-(5-azaspiro[2.4]heptan-5-yl)-1-propanol

The title compound was prepared by similar manner to Example 7, by use of 3-Bromopropanol. Mass: (M+1), 156

Example 9

5-benzyl-7-methoxy-5-azaspiro[2.4]heptane

5-Benzyl-5-azaspiro[2.4]heptan-7-ol (200 mg) was dissolved into DMF (4 ml) and cooled at 0° C. NaH (120 mg) was added to the reaction and stirred for 10 minutes. To the reaction was added TsOMe (200 mg), the solution was heated at 80° C. for two hours. The reaction was quenched with water and extracted with EtOAc followed by washing with water, then brine and dried over Na$_2$SO$_4$ and evaporated to give the titled product. Mass: (M+1), 158

Example 10

7-methoxy-5-azaspiro[2.4]heptane

The title compound was prepared by similar manner to Example 1, starting from the compound of Example 9. Mass: (M+1), 128

Example 11

10-benzyl-5,8-Oxathiolane-10-azadispiro[2.0.4.3]undecane

5-Benzyl-5-azaspiro[2.4]heptan-7-one (100 mg) was mixed with 2-Mercaptoethanol (300 mg) and TSA (10 mg) in Toluene. The reaction was refluxed overnight with a Dean-Stark adaptor. The reaction was washed with NaHCO$_3$ solution, evaporated and purified on silica gel column to give the titled product. Mass: (M+1), 262

Example 12

5,8-Oxathiolane-10-azadispiro[2.0.4.3]undecane 10-benzyl-5,8-Oxathiolane-10-azadispiro[2.0.4.3]undecane (100 mg) was mixed with Pd—C (80 mg, 10%) and HCOONH$_4$ (110 mg) in EtOH. The reaction was refluxed for 1.5 hour and filtered through Celite and evaporated. The residue was washed through a layer of silica gel to give the titled product. Mass: (M+1), 172

Example 13

5,9-Dioxa-11-azadispiro[2.0.4.3]dodecane

5-Benzyl-5-azaspiro[2.4]heptan-7-one (100 mg) was mixed with 1,3-propanediol (200 mg) and TSA (10 mg) in Toluene. The reaction was refluxed overnight with a Dean-Stark adaptor. The reaction was washed with NaHCO$_3$ solution, evaporated and purified on silica gel column to give 11-benzyl-5,9-Dioxa-11-azadispiro[2.0.4.3]dodecane that was hydrogenated similarly to Example 1 to give the titled product. Mass: (M+1), 170

Example 14

5,9-Dioxa-7,7-dimethyl-11-azadispiro[2.0.4.3]dodecane

The title compound was prepared by similar manner to Example 13, starting from the compound of 2,2-Dimethyl-1,3-propanediol. Mass: (M+1), 198

Example 15

11-(2-hydroxyethyl)-5,9-Dioxa-11-azadispiro[2.0.4.3]dodecane 5,9-Dioxa-11-azadispiro[2.0.4.3]dodecane (100 mg) was mixed with 2-Bromoethanol (100 mg) and K$_2$CO$_3$ (120 mg) in Acetonitrile. The reaction was refluxed overnight and filtered, the filtrate was evaporated and purified on silica gel column to give the titled product. Mass: (M+1), 214

Example 16

11-(2-hydroxyethyl)-5,9-Dioxa-7,7-dimethyl-11-azadispiro[2.0.4.3]dodecane 5,9-Dioxa-7,7-dimethyl-11-azadispiro[2.0.4.3]dodecane (100 mg) was mixed with 2-Bromoethanol (100 mg) and $K_2CO_3$ (120 mg) in Acetonitrile. The reaction was refluxed overnight and filtered, the filtrate was evaporated and purified on silica gel column to give the titled product. Mass: (M+1), 242

Example 17

10-(3-amino-5-triflouro-phenyl)-5,8-Dioxa-10-azadispiro[2.0.4.3]undecane

3-Bromo-5-trifouroaniline (200 mg) was mixed with DIPEA (1.5 eq) in DCM (10 ml) at 0° C. To the reaction was added benzylchloroformate (1.1 eq) and stirred at RT for one hour. The reaction was washed with water, brine and dried over $Na_2SO_4$ then evaporated. The residue was purified by column chromatography to give the product (190 mg) that was mixed with 5,8-Dioxa-10-azadispiro[2.0.4.3]undecane (75 mg), Pd(dbda)3 16 mg), X-Phos (28 mg) and t-BuONa (50 mg) in toluene (15 ml). The reaction was heated at 60° C. overnight and evaporated and purified on silica gel column to give the 10-(3-CBZ-amino-5-triflouro-phenyl)-5,8-Dioxa-10-azadispiro[2.0.4.3]undecane (80 mg). This product was mixed with Pd—C (40 mg, 10%), $HCOONH_4$ (160 mg) and MeOH (10 ml). The reaction was refluxed for one hour and filtered through Celite and evaporated. The residue was mixed with water and extracted with EtOAc then purified with silica gel column to give the titled product. Mass: (M+1), 315

Example 18

5-(3-amino-5-triflouro-phenyl)-5-azaspiro[2.4]heptan-7-one

The title compound was prepared by similar manner to Example 3, starting from the compound of Example 17. Mass: (M+1), 271

Example 19

5-(3-amino-5-triflouro-phenyl)-5-azaspiro[2.4]heptan-7-ol

The title compound was prepared by similar manner to Example 5, starting from the compound of Example 18. Mass: (M+1), 273

Example 20

N-(3-chloro-4-fluorophenyl)-7-methoxy-6-[3-(5,8-Dioxa-10-azadispiro[2.0.4.3]undecane) propoxy] quinazolin-4-amine 2-Amino-4-methoxy-5-benzyloxybenzamide (JMC, 20, 146) (5 g) was mixed with triethylorthoformate (15 ml) and refluxed overnight. The reaction solution was cooled and triturated with EtOAc (40 ml) then filtered to give 7-methoxy-6-benzyloxyquinazolone (3.2 g). This product was mixed with DIPEA (15 ml) and to the solution was added $POCl_3$ (3 ml) slowly. The reaction mixture was refluxed for 30 minutes and cooled, then poured into a stirred mixture of ice and $CHCl_3$. The solution was further extracted with $CHCl_3$ three times and washed with $H_2O$ followed by brine, dried over $Na_2SO_4$ and evaporated to give a light brown solid as the chloride for next step without further purification.

The above chloride (2 g) was mixed with 3-chloro-4-flouroaniline (1.3 g) in 2-propanol (30 ml) and the reaction was refluxed for 2 hours and cooled to RT. The precipitate was filtered and mixed with TFA (4 ml) and refluxed for 1 hour. The solvent was evaporated under reduced pressure and the residue was washed with EtOAc to furnish N-(3-chloro-4-fluorophenyl)-7-methoxy-6-hydroxy-quinazolin-4-amine (1.3 g) that was mixed with $K_2CO_3$ (1.1 g) and 3-bromopropanol (850 μL) in DMF (5 ml). The reaction was heated at 80° C. overnight and poured into water and the precipitate was filtered to give N-(3-chloro-4-fluorophenyl)-7-methoxy-6-(2-hydroxyethoxy)-quinazolin-4-amine (1 g). This hydroxy compound (350 mg) was mixed with DIPEA (350 μL) in DCM (10 ml) and cooled at 0° C., to the mixture was added MsCl (85 μL) and stirred for 2 hours. The reaction was evaporated with silica gel (2 g) and purified with silica gel column, then mixed with 5,8-Dioxa-10-azadispiro[2.0.4.3]undecane (B) (120 mg) and DIPEA (120 μL) in 2-propanol (10 ml). The reaction was refluxed overnight and evaporated then purified with silica gel column to give the titled product. Mass: (M+1), 515

Example 21

N-(3-chloro-4-fluorophenyl)-7-methoxy-6-[2-(5,8-Dioxa-10-azadispiro[2.0.4.3]undecane)ethoxy] quinazolin-4-amine The title compound was prepared by similar manner to Example 20, by using 2-bromoethanol instead of 3-bromopropanol. Mass: (M+1), 501

Example 22

N-(3-chloro-4-fluorophenyl)-7-methoxy-6-[3-(5-azaspiro[2.4]heptan-7-one)propoxy]quinazolin-4-amine The title compound was prepared by similar manner to Example 3, starting from the compound of Example 20. Mass: (M+1), 471

Example 23

N-(3-chloro-4-fluorophenyl)-7-methoxy-6-[2-(5-azaspiro[2.4]heptan-7-one)ethoxy]quinazolin-4-amine The title compound was prepared by similar manner to Example 3, starting from the compound of Example 21. Mass: (M+1), 457

Example 24

N-(3-chloro-4-fluorophenyl)-7-methoxy-6-[3-(5-azaspiro[2.4]heptan-7-ol)propoxy]quinazolin-4-amine The title compound was prepared by similar manner to Example 5, starting from the compound of Example 22. Mass: (M+1), 473

Example 25

N-(3-chloro-4-fluorophenyl)-7-methoxy-6-[2-(5-azaspiro[2.4]heptan-7-ol)ethoxy]quinazolin-4-amine The title compound was prepared by similar manner to Example 5, starting from the compound of Example 23. Mass: (M+1), 459

Example 26

N-(3-chloro-4-fluorophenyl)-7-methoxy-6-[3-(7-methoxy-5-azaspiro[2.4]heptane)propoxy]quinazolin-4-amine The title compound was prepared by similar manner to Example 9, starting from the compound of Example 24. Mass: (M+1), 487

Example 27

N-(3-chloro-4-fluorophenyl)-7-methoxy-6-[2-(7-methoxy-5-azaspiro[2.4]heptane)ethoxy]quinazolin-4-amine The title compound was prepared by similar manner to Example 9, starting from the compound of Example 25. Mass: (M+1), 473

Example 28

N-(3-ethynylphenyl)-7-methoxy-6-[2-(5,8-Dioxa-10-azadispiro[2.0.4.3]undecane)ethoxy]quinazolin-4-amine Ethylene glycol (30 ml) was mixed with pyridine (8 ml) and cooled at 0° C. To the mixture was added benzol chloride (7.5 ml) and stirred for 4 hours. The reaction was mixed with EtOAc and acidified with 2N HCl followed by washing with water, then brine and dried over $Na_2SO_4$ and evaporated for next step without further purification.

The above product (4.6 g) was mixed with DIPEA (6.1 ml) in DCM (30 ml) and cooled at 0° C. for 15 minutes. MsCl (2.3 ml) was added into the solution and stirred for 40 minutes, the reaction was washed with $NaHCO_3$ solution followed by washing with water, then brine and dried over $Na_2SO_4$ and evaporated to give the mesylate product for next step without further purification. Ethyl 3-hydroxy-4-methoxybenzonate (3.4 g) was mixed with above mesylate product and $K_2CO_3$ in DMF (20 ml), the reaction was heated at 80° C. for two hours. The solvent was removed under reduced pressure and extracted with EtOAc followed by washing with water, then brine and dried over $Na_2SO_4$ and evaporated to give 3-(2-benzoyloxy)ethoxy-4-methoxy-ethyl benzoate (4 g) for next step without further purification.

The above benzoate (2.5 g) was dissolved into acetic acid (4 ml) and stirred at 0° C. To the reaction was added $HNO_3$ (60%, 8 ml) and stirred at 0° C. for 15 minutes, then stirred at RT for 30 minutes. The reaction was poured into ice-water and the precipitate was filtered to give a yellow solid that was mixed with Iron powder (2 g) and $NH_4Cl$ (250 mg) in EtOH (30 ml). The reaction was refluxed for 2 hours and filtered through Celite and evaporated, then extracted with EtOAc followed by washing with water, then brine and dried over $Na_2SO_4$ and evaporated to give ethyl 2-amino-4-methoxy-5-(2-benzoyloxy)ethoxy benzoate (2 g) for next step without further purification. This benzoate compound (2 g) was mixed with $HCOONH_4$ (1.5 g) in $HCONH_2$ (3 ml) and heated at 170° C. overnight. The reaction was cooled and poured into water (15 ml) and the solid was filtered and dried at 120° C. for 4 hours, then it was mixed with DIPEA (10 ml) and to the solution was added $POCl_3$ (2 ml) slowly. The reaction mixture was refluxed for 30 minutes and cooled, then poured into a stirred mixture of ice and $CHCl_3$. The solution was further extracted with $CHCl_3$ three times and washed with $H_2O$ followed by brine, dried over $Na_2SO_4$ and evaporated to give 6-(2-benzoyloxy)ethoxy-7-methoxy-4-chloro quinazoline for next step without further purification.

The above chloride (1 g) was mixed with 3-ethynylaniline (0.5 g) in 2-propanol (10 ml) and the reaction was refluxed for 2 hours and cooled to RT. The precipitate was filtered and mixed with KOH (500 mg), $H_2O$ (1 ml) and MeOH (10 ml), then stirred at RT overnight. The reaction was evaporated and extracted with EtOAc followed by washing with water, then brine and dried over $Na_2SO_4$ and purified with silica gel column to give N-(3-ethynylphenyl)-7-methoxy-6-(2-hydroxy)ethoxy-quinazolin-4-amine (400 mg). This compound (350 mg) was mixed with DIPEA (350 μL) in DCM (10 ml) and cooled at 0° C., to the mixture was added MsCl (85 μL) and stirred for 2 hours. The reaction was evaporated with silica gel (2 g) and purified with silica gel column, then mixed with 5,8-Dioxa-10-azadispiro[2.0.4.3]undecane (B) (120 mg) and DIPEA (120 μL) in 2-propanol (10 ml). The reaction was refluxed overnight and evaporated then purified with silica gel column to give the titled product. Mass: (M+1), 473

Example 29

N-(3-ethynylphenyl)-7-methoxy-6-[2-(5-azaspiro[2.4]heptan-7-one)ethoxy]quinazolin-4-amine The title compound was prepared by similar manner to Example 3, starting from the compound of Example 28. Mass: (M+1), 429

Example 30

N-(3-ethynylphenyl)-7-methoxy-6-[2-(5-azaspiro[2.4]heptan-7-ol)ethoxy]quinazolin-4-amine The title compound was prepared by similar manner to Example 5, starting from the compound of Example 29. Mass: (M+1), 431

Example 31

N-(3-trifluoromethylphenyl)-7-methoxy-6-[2-(5,8-Dioxa-10-azadispiro[2.0.4.3]undecane)ethoxy]quinazolin-4-amine The title compound was prepared by similar manner to Example 21, by using 3-triflouromethylaniline instead of 3-chloro-4-flouroaniline. Mass: (M+1), 517

Example 32

N-(3-bromophenyl)-7-methoxy-6-[2-(5,8-Dioxa-10-azadispiro[2.0.4.3]undecane)ethoxy]quinazolin-4-amine The title compound was prepared by similar manner to Example 21, by using 3-bromoaniline instead of 3-chloro-4-flouroaniline. Mass: (M+1), 527

Example 33

N-(3,4-dichlorophenyl)-7-methoxy-6-[2-(5,8-Dioxa-10-azadispiro[2.0.4.3]undecane)ethoxy]quinazolin-4-amine The title compound was prepared by similar manner to Example 21, by using 3,4-dichloroaniline instead of 3-chloro-4-flouroaniline. Mass: (M+1), 517

Example 34

N-(3-chloro-4-fluorophenyl)-7-methoxy-6-[3-(5,8-Oxathiolane-10-azadispiro[2.0.4.3]undecane)propoxy]quinazolin-4-amine The title compound was prepared by similar manner to Example 11, starting from the compound of Example 22. Mass: (M+1), 515

Example 35

N-(2-fluoro-4-bromophenyl)-6-methoxy-7-[3-(5,8-Dioxa-10-azadispiro[2.0.4.3]undecane)propoxy]quinazolin-4-amine The title compound was prepared by similar manner to Example 20, starting from the compound of 2-Amino-5-methoxy-4-benzyloxybenzamide (JMC, 20, 146) and using 2-fluoro-4-bromoaniline. Mass: (M+1), 559

Example 36

N-(2-fluoro-4-bromophenyl)-6-methoxy-7-[2-(5,8-Dioxa-10-azadispiro[2.0.4.3]undecane)ethoxy]quinazolin-4-amine The title compound was prepared by similar manner to Example 35, by using 2-bromoethanol. Mass: (M+1), 545

Example 37

N-(3-chloro-4-fluorophenyl)-7-methoxy-6-[2-(5,8-Oxathiolane-10-azadispiro[2.0.4.3]undecane)ethoxy]quinazolin-4-amine The title compound was prepared by similar manner to Example 34, starting from the compound of Example 23. Mass: (M+1), 517

Example 38

N-(3-chloro-4-fluorophenyl)-7-methoxy-6-[2-(5,9-Dioxa-11-azadispiro[2.0.4.3]dodecane)ethoxy]quinazolin-4-amine The title compound was prepared by similar manner to Example 13, starting from the compound of Example 23. Mass: (M+1), 515

Example 39

N-(3-chloro-4-fluorophenyl)-7-methoxy-6-[2-(5,9-Dioxa-7,7-dimethyl-11-azadispiro[2.0.4.3]dodecane)ethoxy]quinazolin-4-amine The title compound was prepared by similar manner to Example 14, starting from the compound of Example 23. Mass: (M+1), 543

Example 40

N-(3-chloro-4-fluorophenyl)-7-methoxy-6-[3-(5,9-Dioxa-11-azadispiro[2.0.4.3]dodecane)propoxy]quinazolin-4-amine The title compound was prepared by similar manner to Example 13, starting from the compound of Example 22. Mass: (M+1), 529

Example 41

N-(3-chloro-4-fluorophenyl)-7-methoxy-6-[3-(5,9-Dioxa-7,7-dimethyl-11-azadispiro[2.0.4.3]dodecane)propoxy]quinazolin-4-amine The title compound was prepared by similar manner to Example 14, starting from the compound of Example 22. Mass: (M+1), 557

Example 42

N-(3-chloro-4-fluorophenyl)-7-methoxy-6-[3-(5-azaspiro[2.4]heptane)propoxy]quinazolin-4-amine This compound was prepared by similar manner to Example 20, by using 5-azaspiro[2.4]heptane instead of 5,8-Dioxa-10-azadispiro[2.0.4.3]undecane (B). Mass: (M+1), 457

Example 43

N-(3-chloro-4-fluorophenyl)-7-methoxy-6-[2-(5-azaspiro[2.4]heptane)ethoxy]quinazolin-4-amine This compound was prepared by similar manner to Example 21, by using 5-azaspiro[2.4]heptane instead of 5,8-Dioxa-10-azadispiro[2.0.4.3]undecane (B). Mass: (M+1), 443

Example 44

5-benzyl-7-methylene-5-azaspiro[2.4]heptane 5-benzyl-5-azaspiro[2.4]heptan-7-one (300 mg) was dissolved into anhydrous tetrahydrofuran (10 ml) and Nysted reagent (1.5 eq, 20% solution) was added to the reaction. The reaction was stirred at RT for two days and quenched with NH$_4$Cl solution and extracted with EtOAc followed by washing with water, then brine and dried over Na$_2$SO$_4$ and purified with silica gel column to give the titled compound. Mass: (M+1), 200

Example 45

7-methylene-5-azaspiro[2.4]heptane

The title compound was prepared by similar manner to Example 12, starting from the compound of 5-benzyl-7-methylene-5-azaspiro[2.4]heptane. Mass: (M+1), 110

Examples of Salt Formation:

Compound from example 20 (100 mg) was dissolved into EtOAc (1 ml) and to the solution was added 2N HCl/Ether solution (0.5 ml). The solution was evaporated to give a off white solid as its HCl salt.

The other pharmaceutical acceptable salts, such as hydrobromic, sulphuric, nitric, phosphoric acid; or succinic, maleic, acetic, fumaric, citic, tartaric, benzoic, p-toluenesulfonic, methanesulfonic, naphthalenesulfonic acid salt can be prepared in the similar manner.

EXAMPLES OF FORMULATION

The following are the examples of the formulations and these are purely illustrative and in no way to be interpreted as restrictive.

Formulation Example 1

Each capsule contains:

| Compound Example 20 | 100.0 mg |
|---|---|
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | 150.0 mg |

Formulation Example 2

A solution contains:

| Compound Example 20 | 1 to 10 g |
|---|---|
| Acetic acid or sodium hydroxide | 0.5 to 1 g |
| Ethyl p-hydroxybenzoate | 0.1 g |
| Purified water | 88.9 to 98.4 g |
| | 100.0 g |

Formulation Example 3

A powder for admixing with feedstuff contains:

| Compound Example 20 | 1 to 10 g |
|---|---|
| Corn starch | 98.5 to 89.5 g |
| Light anhydrous silicic acid | 0.5 g |
| | 100.0 g |

What is claimed is:
1. A spiro compound of formula I

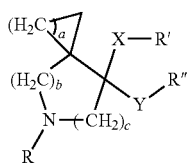

Formula I

Wherein
a is 1, 2, 3, 4 or 5;
b and c are each independently 1, 2, or 3;
When X and Y are selected from (i) X combines Y to be an oxygen or methylene, (ii) X is hydrogen, Y is hydrogen, (iii) X is hydrogen, Y is hydroxy or its optical isomer; R' and R" are not presented;

When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents;

R is selected from:

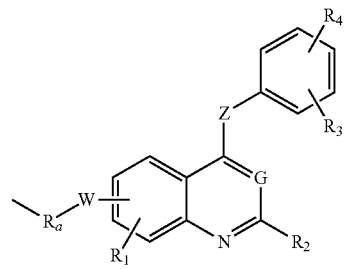

and G is N $R_a$ is selected from lower alkylenyl, lower alkenlenyl or lower alkynlenyl;

W is selected from O, S, —$NR_c$ or —$CHR_c$;

Z is selected from O, S, —$NR_d$ or —$CHR_d$;

$R_c$ is selected from H, lower alkyl;

$R_d$ is selected from H, lower alkyl, amino or alkylamino;

$R_1$, $R_3$, and $R_4$ are each independently selected from H, halogen, halogeno-lower alkyl, lower alkyl, lower alkoxy, lower alkoxyalkoxy, lower alkenyl, or lower alkynyl;

$R_2$ is selected from H, halogen, halogeno-lower alkyl or lower alkyl;

Or a pharmaceutically acceptable salt thereof.

2. A compound of Formula I according to claim 1, wherein
a is 1, 2, 3, 4 or 5;
b and c are each independently 1, 2, or 3;
When X and Y are selected from (i) X combines Y to be an oxygen or methylene, (ii) X is hydrogen, Y is hydrogen, (iii) X is hydrogen, Y is hydroxy or its optical isomer; R' and R" are not presented; these moieties are selected from ketone, methylene as well as hydroxy and its optical isomers;

When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents;

R is selected from:

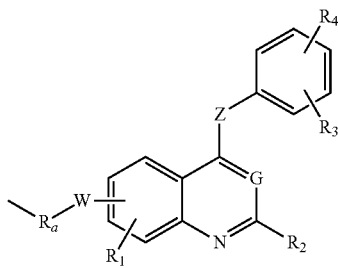

and G is N

R$_a$ is selected from lower alkylenyl, lower alkenlenyl or lower alkynlenyl;
W is selected from O, S, —NR$_c$ or —CHR$_c$;
Z is selected from O, S, —NR$_d$ or —CHR$_d$;
R$_c$ is selected from H, lower alkyl;
R$_d$ is selected from H, lower alkyl, amino or alkylamino;
R$_1$, R$_3$, and R$_4$ are each independently selected from H, halogen, halogeno-lower alkyl, lower alkyl, lower alkoxy, lower alkoxyalkoxy, lower alkenyl, or lower alkynyl;
R$_2$ is selected from H, halogen, halogeno-lower alkyl or lower alkyl;
Or a pharmaceutically acceptable salt thereof.

3. A compound of Formula I according to claim 1, wherein
a is 1;
b and c are each independently 1;
When X and Y are selected from (i) X combines Y to be an oxygen or methylene, (ii) X is hydrogen, Y is hydrogen, (iii) X is hydrogen, Y is hydroxy or its optical isomer; R' and R" are not presented; these moieties are selected from ketone, methylene as well as hydroxy and its optical isomers;
When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents;
R is selected from:

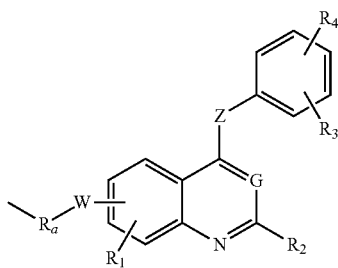

and G is N
R$_a$ is lower alkylenyl;
W is selected from O, S, —NR$_c$ or —CHR$_c$;
Z is selected from O, S, —NR$_d$ or —CHR$_d$;
R$_c$ is selected from H, lower alkyl;
R$_d$ is selected from H, lower alkyl, amino or alkylamino;
R$_1$, R$_3$, and R$_4$ are each independently selected from H, halogen, halogeno-lower alkyl, lower alkyl, lower alkoxy, lower alkoxyalkoxy, lower alkenyl, or lower alkynyl;
R$_2$ is selected from H, halogen, halogeno-lower alkyl or lower alkyl;
Or a pharmaceutically acceptable salt thereof.

4. A compound of Formula I according to claim 1, wherein
a is 1;
b and c are each independently 1;
When X and Y are selected from (i) X combines Y to be an oxygen or methylene, (ii) X is hydrogen, Y is hydrogen, (iii) X is hydrogen, Y is hydroxy or its optical isomer; R' and R" are not presented; these moieties are selected from ketone, methylene as well as hydroxy and its optical isomers;
When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents;
R is selected from:

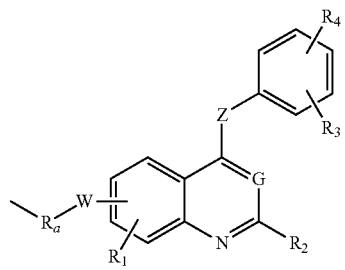

and G is N
R$_a$ is lower alkylenyl;
W is O;
Z is selected from O, S, —NR$_d$ or —CHR$_d$;
R$_d$ is selected from H, lower alkyl, amino or alkylamino;
R$_1$, R$_3$, and R$_4$ are each independently selected from H, halogen, halogeno-lower alkyl, lower alkyl, lower alkoxy, lower alkoxyalkoxy, lower alkenyl, or lower alkynyl;
R$_2$ is selected from H, halogen, halogeno-lower alkyl or lower alkyl;
Or a pharmaceutically acceptable salt thereof.

5. A compound of Formula I according to claim 1, wherein
a is 1;
b and c are each independently 1;
When X and Y are selected from (i) X combines Y to be an oxygen or methylene, (ii) X is hydrogen, Y is hydrogen, (iii) X is hydrogen, Y is hydroxy or its optical isomer; R' and R" are not presented; these moieties are selected from ketone, methylene as well as hydroxy and its optical isomers;
When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring, may be unsubstituted or substituted independently by up to three substituents;
R is selected from:

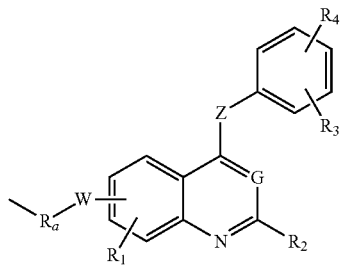

and G is N
$R_a$ is lower alkylenyl;
W is O;
Z is —$NR_d$;
$R_d$ is H;
$R_1$, $R_3$, and $R_4$ are each independently selected from H, halogen, halogeno-lower alkyl, lower alkyl, lower alkoxy, lower alkoxyalkoxy, lower alkenyl, or lower alkynyl;
$R_2$ is selected from H, halogen, halogeno-lower alkyl or lower alkyl;
Or a pharmaceutically acceptable salt thereof.

6. A compound of Formula I according to claim 1, wherein a is 1;
b and c are each independently 1;
When X and Y are selected from (i) X combines Y to be an oxygen or methylene, (ii) X is hydrogen, Y is hydrogen, (iii) X is hydrogen, Y is hydroxy or its optical isomer; R' and R" are not presented; these moieties are selected from ketone, methylene as well as hydroxy and its optical isomers;
When X and Y are selected from (iv) X is hydrogen, Y is O, S or its optical isomer position, (v) X and Y are both O or S, or (vi) X is O and Y is S; R' and R" are each independently halogeno-lower alkyl, lower alkyl, lower alkoxy, hydroxy, lower alkylhydroxy; optionally R' and R" combine to form a 5 to 7 membered ring with X, Y and the spiro carbon which ring are selected from alkoxy or its optical isomers, and alkyl or cyclic ketal, thioketal, thioxolane which may be unsubstituted or substituted with lower alkyl, aryl or heterocyclyl;
R is selected from:

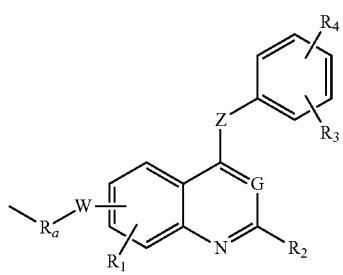

and G is N
$R_a$ is lower alkylenyl;
W is O;
Z is —$NR_d$;
$R_d$ is H;
$R_1$, $R_3$, and $R_4$ are each independently halogen, lower alkyl or lower alkoxy;
$R_2$ is H or fluorine;
Or a pharmaceutically acceptable salt thereof.

7. A compound of Formula I according to claim 1 selected from:

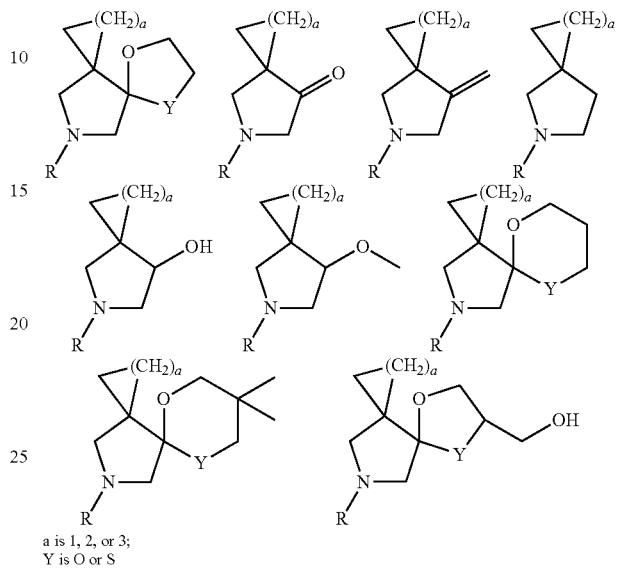

a is 1, 2, or 3;
Y is O or S

R is selected from: - - - : Substituting position

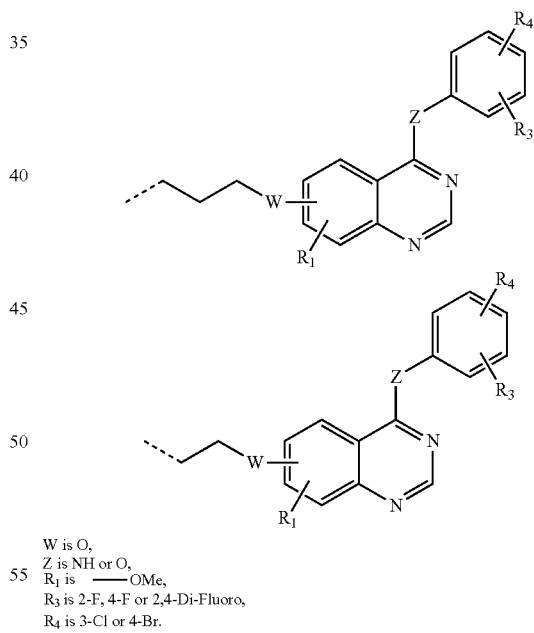

W is O,
Z is NH or O,
$R_1$ is ——OMe,
$R_3$ is 2-F, 4-F or 2,4-Di-Fluoro,
$R_4$ is 3-Cl or 4-Br.

Or a pharmaceutically acceptable salt thereof.
8. A compound of Formula I according to claim 1 selected from:
N-(3-chloro-4-fluorophenyl)-7-methoxy-6-[3-(5,8-Dioxa-10-azadispiro[2.0.4.3]undecane)propoxy]quinazolin-4-amine
N-(3-chloro-4-fluorophenyl)-7-methoxy-6-[2-(5,8-Dioxa-10-azadispiro[2.0.4.3]undecane)ethoxy]quinazolin-4-amine N-(3-chloro-4-fluorophenyl)-7-methoxy-6-[3-(5-azaspiro[2.4]heptan-7-one)propoxy]quinazolin-4-amine
N-(3-chloro-4-fluorophenyl)-7-methoxy-6-[2-(5-azaspiro[2.4]heptan-7-one)ethoxy]quinazolin-4-amine
N-(3-chloro-4-fluorophenyl)-7-methoxy-6-[3-(5-azaspiro[2.4]heptan-7-ol)propoxy]quinazolin-4-amine
N-(3-chloro-4-fluorophenyl)-7-methoxy-6-[2-(5-azaspiro[2.4]heptan-7-ol)ethoxy]quinazolin-4-amine
N-(3-chloro-4-fluorophenyl)-7-methoxy-6-[3-(7-methoxy-5-azaspiro[2.4]heptane)propoxy]quinazolin-4-amine
N-(3-chloro-4-fluorophenyl)-7-methoxy-6-[2-(7-methoxy-5-azaspiro[2.4]heptane)ethoxy]quinazolin-4-amine
N-(3-ethynylphenyl)-7-methoxy-6-[2-(5,8-Dioxa-10-azadispiro[2.0.4.3]undecane)ethoxy]quinazolin-4-amine
N-(3-ethynylphenyl)-7-methoxy-6-[2-(5-azaspiro[2.4]heptan-7-one)ethoxy]quinazolin-4-amine
N-(3-ethynylphenyl)-7-methoxy-6-[2-(5-azaspiro[2.4]heptan-7-ol)ethoxy]quinazolin-4-amine
N-(3-trifluoromethylphenyl)-7-methoxy-6-[2-(5,8-Dioxa-10-azadispiro[2.0.4.3]undecane)ethoxy]quinazolin-4-amine
N-(3-bromophenyl)-7-methoxy-6-[2-(5,8-Dioxa-10-azadispiro[2.0.4.3]undecane)ethoxy]quinazolin-4-amine
N-(3,4-dichlorophenyl)-7-methoxy-6-[2-(5,8-Dioxa-10-azadispiro[2.0.4.3]undecane)ethoxy]quinazolin-4-amine
N-(3-chloro-4-fluorophenyl)-7-methoxy-6-[3-(5,8-Oxathiolane-10-azadispiro[2.0.4.3]undecane)propoxy]quinazolin-4-amine
N-(2-fluoro-4-bromophenyl)-6-methoxy-7-[3-(5,8-Dioxa-10-azadispiro[2.0.4.3]undecane)propoxy]quinazolin-4-amine
N-(2-fluoro-4-bromophenyl)-6-methoxy-7-[2-(5,8-Dioxa-10-azadispiro[2.0.4.3]undecane)ethoxy]quinazolin-4-amine
N-(3-chloro-4-fluorophenyl)-7-methoxy-6-[2-(5,8-Oxathiolane-10-azadispiro[2.0.4.3]undecane)ethoxy]quinazolin-4-amine
N-(3-chloro-4-fluorophenyl)-7-methoxy-6-[2-(5,9-Dioxa-11-azadispiro[2.0.4.3]dodecane)ethoxy]quinazolin-4-amine
N-(3-chloro-4-fluorophenyl)-7-methoxy-6-[2-(5,9-Dioxa-7,7-dimethyl-11-azadispiro[2.0.4.3]dodecane)ethoxy]quinazolin-4-amine
N-(3-chloro-4-fluorophenyl)-7-methoxy-6-[3-(5,9-Dioxa-11-azadispiro[2.0.4.3]dodecane)propoxy]quinazolin-4-amine
N-(3-chloro-4-fluorophenyl)-7-methoxy-6-[3-(5,9-Dioxa-7,7-dimethyl-11-azadispiro[2.0.4.3]dodecane)propoxy]quinazolin-4-amine
N-(3-chloro-4-fluorophenyl)-7-methoxy-6-[3-(5-azaspiro[2.4]heptane)propoxy]quinazolin-4-amine
N-(3-chloro-4-fluorophenyl)-7-methoxy-6-[2-(5-azaspiro[2.4]heptane)ethoxy]quinazolin-4-amine Or a pharmaceutically acceptable salt thereof.

9. A pharmaceutical composition comprising a compound of claim 1 and a pharmaceutically acceptable salt or a pharmaceutically acceptable carrier.

10. A pharmaceutical composition comprising a compound of claim 8 and a pharmaceutically acceptable salt or a pharmaceutically acceptable carrier.

* * * * *